(12) United States Patent
Karapetyan

(10) Patent No.: US 9,226,807 B1
(45) Date of Patent: Jan. 5, 2016

(54) TOOTH CLEANING DEVICE

(71) Applicant: Armen Karapetyan, Los Angeles, CA (US)

(72) Inventor: Armen Karapetyan, Los Angeles, CA (US)

(*) Notice: Subject to any disclaimer, the term of this patent is extended or adjusted under 35 U.S.C. 154(b) by 0 days.

(21) Appl. No.: 14/544,148

(22) Filed: Dec. 2, 2014

(51) Int. Cl.
A46B 11/06 (2006.01)
A61C 17/02 (2006.01)

(52) U.S. Cl.
CPC ............ A61C 17/0214 (2013.01); A46B 11/066 (2013.01); A46B 11/06 (2013.01)

(58) Field of Classification Search
CPC combination set(s) only.
See application file for complete search history.

(56) References Cited

U.S. PATENT DOCUMENTS

| | | | | |
|---|---|---|---|---|
| 1,479,275 A * | 1/1924 | Beil | | 401/287 |
| 2,855,619 A * | 10/1958 | Graham | | 401/46 |
| 3,593,707 A * | 7/1971 | Pifer | | 601/163 |
| 5,142,723 A * | 9/1992 | Lustig et al. | | 15/22.1 |
| 5,500,973 A * | 3/1996 | Phelan | | 15/29 |
| 5,683,192 A * | 11/1997 | Kilfoil | | 401/289 |
| 5,697,784 A * | 12/1997 | Hafele et al. | | 433/85 |
| 5,876,135 A * | 3/1999 | Wang et al. | | 401/46 |
| 6,991,460 B2 * | 1/2006 | Karapetyan | | 433/98 |
| 8,141,563 B2 * | 3/2012 | De Masi, Sr. | | 132/309 |
| 8,801,316 B1 * | 8/2014 | Abedini | | 401/289 |

* cited by examiner

Primary Examiner — David Walczak

(57) ABSTRACT

The present tooth cleaning device generally comprises a controllable fluid distributer coupled with the sink/bath faucet and by first connecting element with the first end of the flexible tube, the second end of which is coupled with the projection of the handle portion of the brush portion, which also includes the head portion comprising the bristle portion, fluid channel, and at least one aperture in the bristle portion of the brush head portion.

1 Claim, 5 Drawing Sheets

TOOTH CLEANING DEVICE

FIELD OF THE INVENTION

This invention is generally related to the tooth cleaning apparatus, and more particularly to the dental hygiene devices with a spray (fluid stream, jet) providing an appliance of liquid spray or jet/stream action for tooth cleaning with the brushing action. The brush cleans a plaque from tooth surfaces and the jet flushes away the plaque debris.

BACKGROUND OF THE INVENTION

It is also known, that major incidences of tooth decay and of periodontal disease occur in interproximal areas such as crevices between adjacent teeth and the pits and fissures of the occlusal surfaces. Cleaning these areas with traditional hand brushing methods generally is unsatisfactory, with ineffective removal of residue and of dental plaque, and resulting in increased susceptibility to tooth decay and periodontal disease. The dental hygiene devices, such as tooth brushes provide gingival stimulation and enhance the peripheral capillary dental circulation, and also conventional hand brushing dental hygiene practices are fairly efficient for cleaning smooth facial and lingual surfaces of the teeth because the bristle tips of a conventional toothbrush can readily access these broad surfaces. The known techniques propose to solve these problems are powered brushes, in which the entire brush head is moved while water or another fluid is emitted from the brush head.

Other prior art techniques are powered brushes in which the brush head has rotating tufts and/or longitudinal (reciprocating) movements of bristles, and liquid jet devices. For example, U.S. Pat. No. 5,142,723 describes a tooth cleaning apparatus having powered brush and spray and includes a housing that provides a manually deployable handle for the device and that houses a motor that drives both a brush agitating drive mechanism, and a liquid dispensing pump mechanism. The housing has a tool mount that interchangably mounts in operable relation with the drive mechanism and with the pump mechanism any one of a dental brush tool and a dental spray tool. The brush tool and the drive mechanism preferably are arranged to agitatingly drive two sets of brush elements and oppositely, preferably with back and forth rotation of individual brush tufts. The motor is powered either by batteries mounted within the housing or from an external power source, has an output shaft a centered on the axis and mechanically coupled to rotate a beveled gear about the axis. The beveled gear is drivingly engaged with a pair of cranking bevel gears and coupled with the output shaft of the motor. The cranking gears are rotatable about a common axis, perpendicular to the axis, by way of shaft screws that mount each gear to a support frame that in turn is seated within the housing. The cranking gears are spaced apart along the axis. A crank rod is pinned to the periphery of the cranking gear and a similar crank rod is pinned to the cranking gear. Each crank rod extends generally along the direction of axis and is rotatably fastened at its end remote from its respective cranking gear to one reciprocating rod respectively. The reciprocating rods extend side-by-side along the direction of axis and are axially slidable relative to the housing.

Such device is very complex and requires a liquid dispensing pump mechanism.

The device by U.S. Pat. No. 6,991,460, provides a multi-brush tooth cleaning apparatus with a spray providing a possibility to clean the teeth with the simultaneous flushing away the plaque debris and includes a fluid inlet tubular means coupled with the sink/bath faucet and with a main controllable valve installed on a stand comprising the major manifold. The stand comprises a fluid line, at least one of a plurality of fluid channels, an appropriate at least one of the same plurality of outlet pipes coupled with an appropriate at least one of the same plurality of the auxiliary controllable valves coupled by the flexible tubes with an appropriate at least one of the same plurality of the mouthpieces (tooth brushes). The outlet pipes are appropriately extended of the fluid line, and each of the outlet pipes is rigidly connected to the appropriate auxiliary controllable valve, comprising a lever intended to close or open the auxiliary controllable valve for fluid flow. Specifically, the multibrush tooth cleaning apparatus provides a family dental hygiene, wherein in the initial state (for example, all tooth brushes are inserted in the appropriate holders and the main controllable valve is closed). At this state, all levers of all auxiliary valves are "down" in the vertical positions, which correspond to their closed position. In this position the eccentric of the lever extends rod of the auxiliary controllable valve, thereby closing valve for fluid flow (the eccentric is coupled with the rod by the appropriate pin). At the time when the user pulls his/her personal tooth brush (for instance, the i-th tooth brush) from the appropriate i-th holder, the i-th lever's spring (not shown) actuates the i-th lever moving it in the its horizontal position, thereby opening the auxiliary controllable valve for fluid flow. Then the user open the faucet's valve, and when the user is ready to spray/jet the fluid to the teeth, he/she open the main controllable valve providing the fluid flow into fluid line. The fluid flows from the opened main controllable valve along the fluid line, through the i-th outlet pipe, opened i-th auxiliary controllable valve, i-th tubular means, fluid passage into handle portion of the i-th tooth brush to the apertures located into bristle area of the bristle portion, and through the apertures of the bristle portion of the i-th tooth brush to the teeth, thereby spraying (sprinkling) the teeth by fluid. When the dental hygiene procedure is completed, the user turns-off (closes) the main controllable valve, closing the fluid line for the fluid flow, and installs the i-th tooth brush in the i-th holder, thereby closing the i-th auxiliary controllable valve.

Such apparatus is complex, requires space and complex installation near sink, and is not efficient for the single person use.

In some other known dental cleaning devices, the dental jet device whose grip member comprises a control means in the form of an adjustment wheel. The adjustment wheel is connected to a rotatable valve body of a valve provided as fluid-flow control means. An amount of fluid which flows through the fluid channel in a given time interval, which fluid is supplied to the mouthpiece of the dental jet device and is adequate for a normal cleaning operation, is adjustable by turning the valve body by means of the adjustment wheel in order to supply this amount of fluid. The amount of fluid is below a maximum possible flow and is selected by the user, is supplied to the mouthpiece of the dental jet device. In order to increase the fluid supply to the mouthpiece after the fluid flow has been adjusted by means of the adjustment wheel, for example in order to remove very persistent residual food particles, the adjustment wheel on the grip member of the known dental jet device should be rotated from a previously selected setting for a desired fluid flow to a setting for an increased fluid flow. As a result the previously selected setting of the adjustment wheel for the previously desired fluid flow adequate for a normal cleaning operation is lost. Moreover, in the known dental-jet device the fluid flow supplied to a mouthpiece cannot be increased beyond the maximum fluid flow dictated by the dimensioning of the fluid channel and the fluid-flow control means. For example, in U.S. Pat. No. 5,697, 784 a dental cleaning device is provided with a mouthpiece and with a grip member having a fluid channel and having a fluid-flow control device located on the brush body, which is adjustable an actuating member, which is movable between different actuating positions to change the amount of fluid supplied to the mouthpiece through the fluid channel, the grip member is provided with activatable parts for temporarily increasing the amount of fluid supplied to the mouthpiece while the instantaneous actuating position of the actuating member for the fluid-flow control device. The grip member comprises a slide knob which is guided so as to be movable in the longitudinal direction of the grip member indicated by the arrow and in a direction opposite thereto, between an "off"-position and an "on"-position. When the slide knob is in the "on"-position the water supply from the tube to the mouthpiece via the grip member is interrupted and when the slide knob is in its "on"-position water supply from the tube to the mouthpiece via the grip member is possible. A push-button included in the slide knob has a part which points away from the grip member and traverses the slide knob. The grip member of the dental jet device has an elongate sleeve-shaped plastic housing comprising a first housing section, situated nearest a mouthpiece, and a second housing section, whose end adjoins the end of the first housing section at the location of the flexible adjustment ring. At its free end the first housing section has an opening through which the interior of an inner tubular housing portion is accessible. A mouthpiece is inserted into the tubular housing portion through the opening to couple this mouthpiece to the grip member in a fluid-transmitting manner. At its free end the second housing section has a bottom. The tubular portion of the first housing section is adjoined by a plastic tubular coupling member located in the first housing section and having a comparatively thick-walled portion into which the end of a mouthpiece can be introduced. At the location of the comparatively thick-walled portion a wire spring is arranged having a circular shape over an angle of substantially 270 degree and having straight end portions which extend substantially parallel to one another and towards the interior of the circular spring. The two spring ends hold a mouthpiece onto the grip member in that the spring ends engage a groove in the mouthpiece. The end of a mouthpiece held by means of the spring then lies against a sealing ring fitted in the comparatively thick-walled portion of the coupling member.

This device is complex too and expensive.

The tooth brush by U.S. Pat. No. 8,141,563 describes the tooth brush combination. The simple design includes a movable flossing head and tong cleaning section. The device provides the locking the flossing head in to place when in use or change the position of the flossing head when needed.

Such device is not complex and not expensive, but is not efficient because it does not provide the liquid jet stream which additionally and effectively cleans the teeth and flushes away the plaque debris.

Thus, there is a great need in the art for the improved tooth cleaning device with a spray (fluid stream, jet), providing convenient, economical and effective cleaning of the teeth with the flushing away the plaque debris.

OBJECT AND ADVANTAGES OF THE INVENTION

Accordingly, several objects and advantages of the present invention are to provide convenient, efficient, economical and effective tooth cleaning device.

It is further object of the invention to increase efficiency of the dental hygiene.

It is still further object of the invention to increase a convenience for routine use of the dental cleaning device.

It is another object of the invention to eliminate necessity of the manual moisturizing of the tooth brush during tooth cleaning process.

It is still another object of the invention to provide convenient and nor complex control of the fluid spray/stream flow.

Still, further objects and advantages will become apparent from a consideration of the ensuing description accompanying drawings.

DESCRIPTION OF THE DRAWING

In order that the invention and the manner in which it is to be performed may be more clearly understood, embodiments thereof will be described by way of example with reference to the attached drawings, of which.

SUMMARY OF THE INVENTION

In view of the foregoing disadvantages inherent in the known prior art, the present invention provides a new tooth cleaning device with a spray/stream eliminating the manual moisturizing of the tooth brush during tooth cleaning process. As such, the general purpose of the present invention, which will be described hereinafter in greater details, is to provide a new tooth cleaning device with a spray/stream, which has many of the advantages of the dental hygiene devices with a spray (stream) mentioned heretofore and many novel features that result in the convenient and efficient tooth cleaning device, which is not anticipated, rendered obvious, suggested or even implied by any of prior art dental hygiene devices, either alone or in any combination thereof. To attain this, the present invention generally comprises a controllable fluid distributer coupled with the sink (bath) faucet and with a tubular portion (tube), which is coupled by a connecting element with the connecting portion of the hollow handle portion of the brush portion or with the connecting portion of the channeled handle portion of the brush portion, and wherein the brush portion additionally to the handle portion comprises brush head portion including the bristle portion, fluid channel, and at least one aperture in the bristle portion of the brush head portion.

DESCRIPTION OF THE PREFERRED EMBODIMENTS

With reference now to the drawings, and particularly to FIGS. 1-8 thereof, an improved tooth cleaning device embodying the principles and concepts of the present invention.

The term "tubular" hereinbelow solely and/or jointly accumulate the meaning, for instance, of the "tube", "pipe", "fluid conductor", "conduit", etc. Therefore, the use at least one of the terms does not exclude the other meanings for the used term, if otherwise not specified.

DESCRIPTION OF THE PREFERRED EMBODIMENTS

Figure 1:
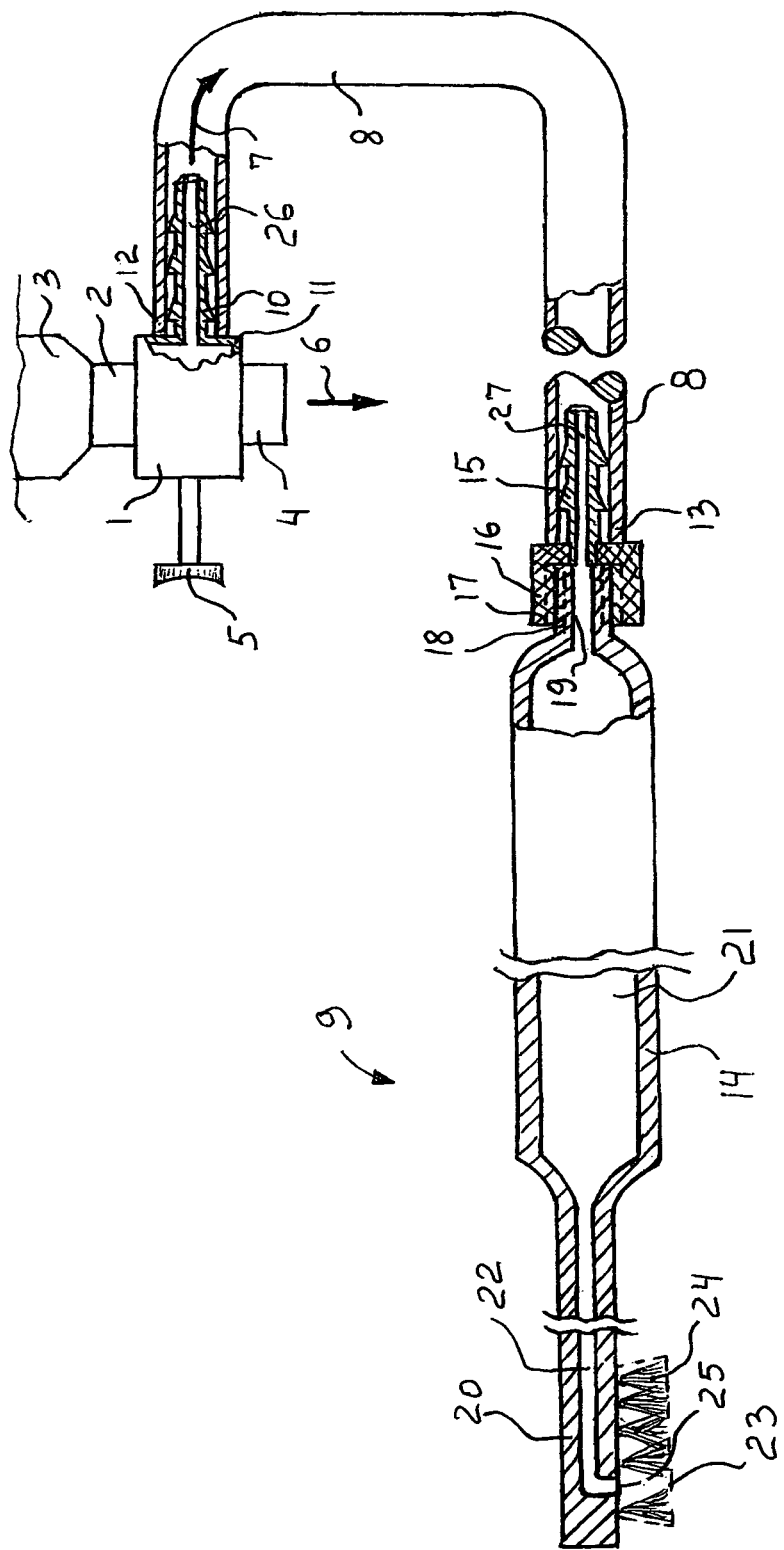
FIG. 1 is a simplified drawing of an improved tooth cleaning device with the hollow handle portion.

In the FIG. 1 are shown the improved tooth cleaning device. The device comprises a controllable distributer 1 for control of the fluid (e.g., such as a water) flow direction. The controllable fluid distributer 1 is coupled with the facet nozzle 2 of the sink (or bath) facet 3. The controllable distributer 1 includes: a distributer nozzle 4, providing fluid flow from the sink facet 3 through the distributer nozzle 2 into the sink (not shown); control organ (switch) 5, providing the switching function, i.e. switching water flow in the direction 6 from the sink facet nozzle 2 in the sink through the distributer nozzle 4, for example, for hands wash, or in the direction 7 for cleaning the teeth (not shown). Also, the improved tooth cleaning device comprises the tubular portion [tube (preferably flexible tube)] 8 and brush portion 9.

Figure 3:
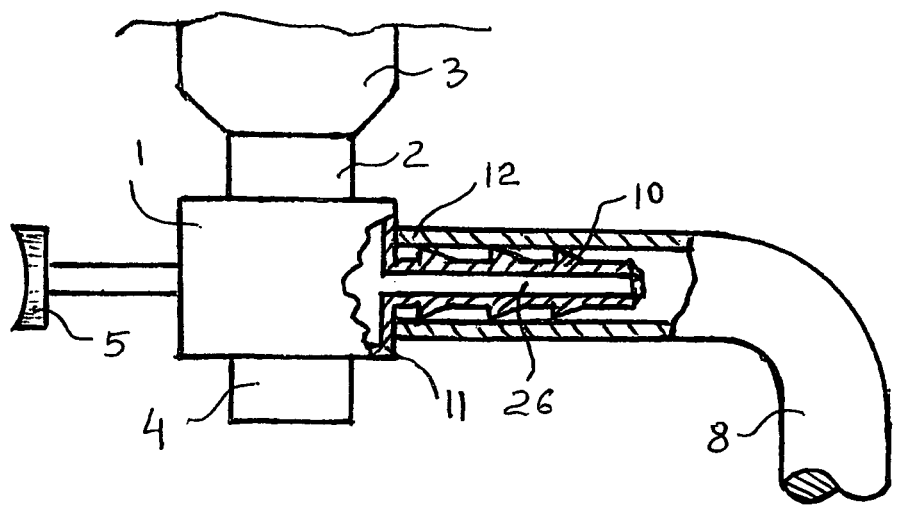
FIG. 3 is a simplified drawings of the first variants of the coupling.

Referring to FIGS. 1 and 3, the controllable distributer 1 also comprises a first connecting element 10, extended from the body 11 of the controllable distributer 1. The first connecting element 10 of the controllable distributer 1 is intended for tight (not leaking) coupling of the controllable distributer 1 with the first end 12 of the tubular portion 8.

The second end 13 of the tubular portion (tube) 8 can be coupled with the brush portion 9 in the same manner as with the controllable distributer 1 [e.g., through the connecting element (not shown) of the handle portion 14 of the brush portion 9, but the preferred variant of the coupling tubular portion 8 with the handle portion 14 of the brush portion 9 is shown in FIG. 1.

Figure 4:
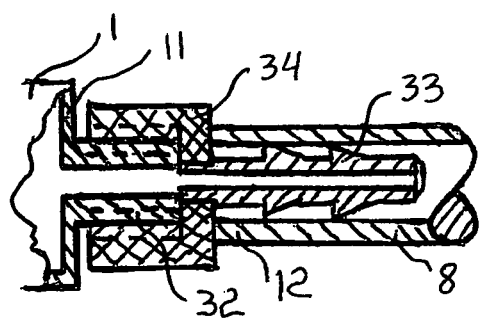
FIG. 4 is a simplified drawings of the second variants of the coupling.

Similarly, the first end 12 of the tubular portion (tube) 8 can be coupled with the controllable distributer 1 in the same manner as with the brush portion 9 [e.g., through the threaded coupling of the projection 32 of the body 11 of controllable distributer 1 with the third connecting element 33 by the second pivotable nut 34, as it is shown in FIG. 4].

According to FIG. 1, the tube 8 includes the second connecting element 15, tightly (not leakage) inserted into second end 13 of the tube (tubular portion) 8. The second connecting element 15 includes a freely pivotable nut 16 comprising the internal thread 17 intended for coupling with the external thread 18 of the projection 19 of the handle portion 14 of the brush portion 9. Any other suitable thread based coupling can be used too, for example, a short thread (not shown) coupling with the flanged (not shown) connecting elements 10 and 15.

Still referring to FIG. 1, the brush portion 9 comprises the handle portion 14 and the head portion 20. The handle portion 9 includes the hollow body 21 and the projection 19, comprising that external thread 18. The head portion 20 includes the head channel 22, the bristle portion 23, comprising bristles 24, and an aperture 25.

Figure 2:
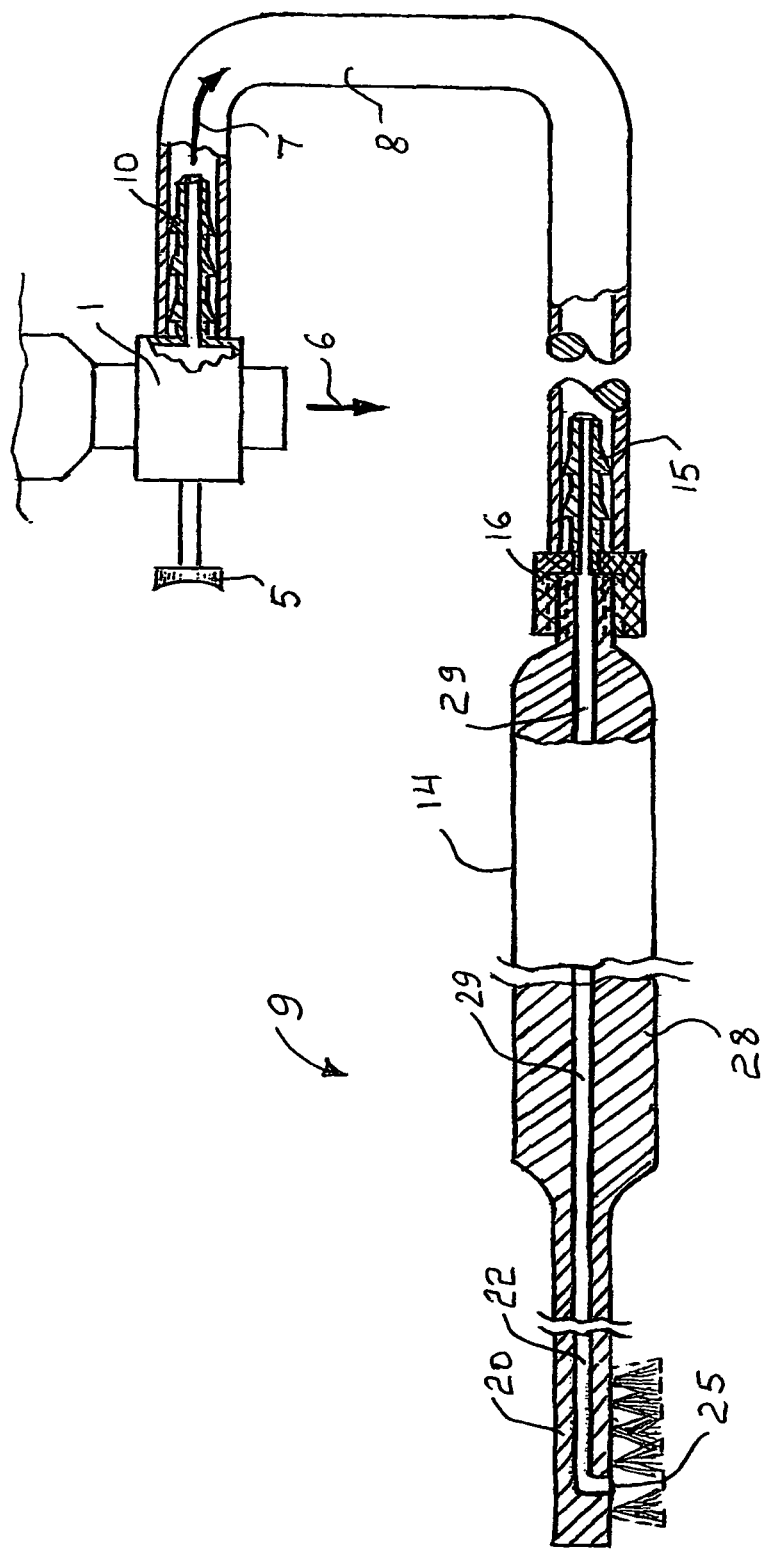
FIG. 2 is a simplified drawing of an improved tooth cleaning device with the channeled handle portion.

The first connecting element 10 and second connecting element 13 include the first connecting element channel 26 and second connecting element channel 27 respectively, both intended for the fluid (water) passage in the direction 7 (FIGS. 1 and 2).

In FIG. 2 is shown the brush portion 9 with the channeled configuration of the handle portion 14, wherein the handle portion 14 comprises the solid (not hollow) body 28 with the handle channel 29, extending from the head channel 22.

FIGS. 1 and 2 describe the hollow (hollowed body 21) or channeled (handle channel 29) configurations, but it can be any suitable configuration and/or geometric form of channel 29 [e.g., square (not shown), triangular (not shown) or conic (not shown) cross-sections of the channel, etc.] and the channel 29 can be so wide (not shown) that it can be perception of the channel as the hollowed body, and wise-versa: the hollow body 21 can include so thick walls (not shown), that it can be perception of the cavity as the channel with the big diameter (or other cross-sectional dimensions).

Also, FIGS. 1 and 2 show the presence of a single aperture 25, but there can be a plurality of apertures (not shown) in the bristle portion 23 of the head portion 20 of the brush portion 9.

Figure 5:
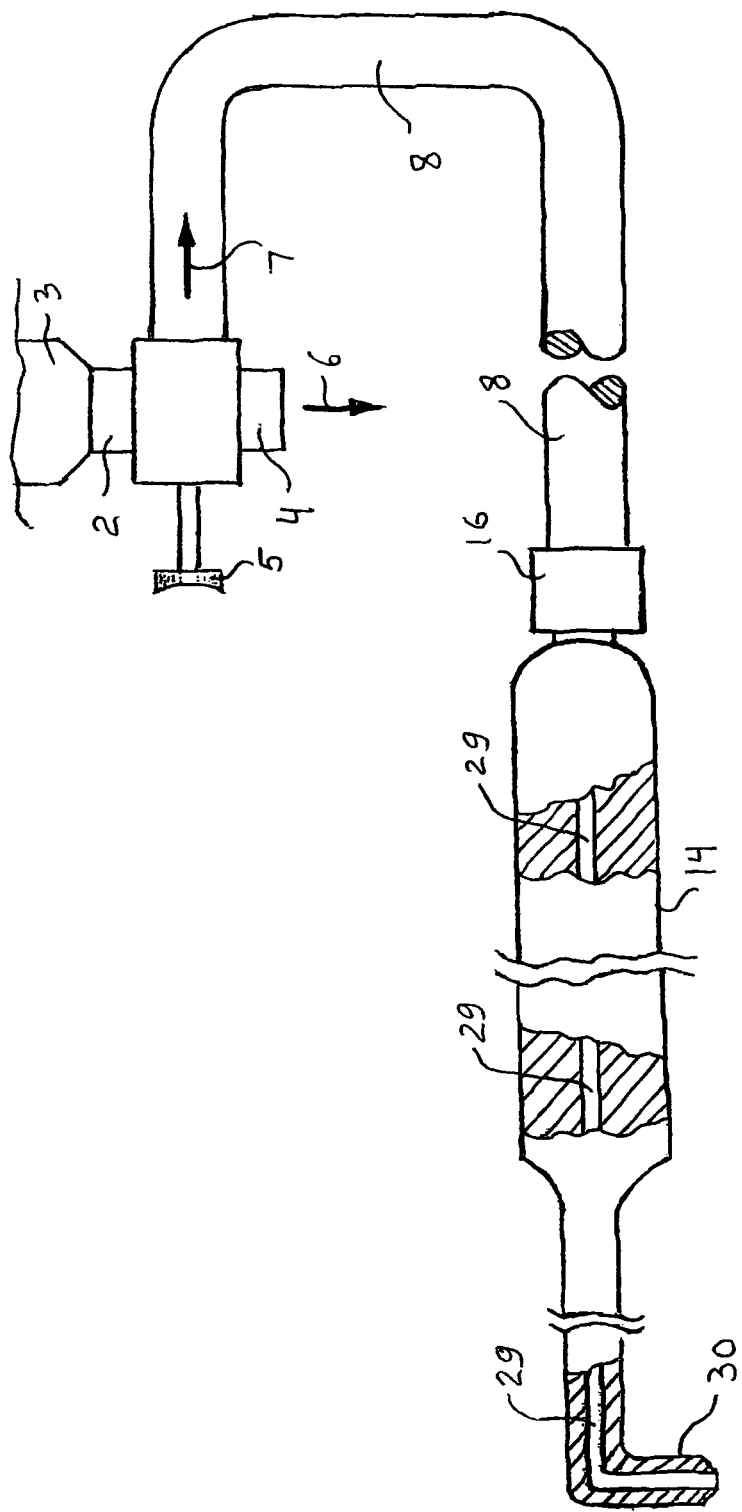
FIG. 5 is a simplified drawing of an improved tooth fluid jet stream cleaning device.

Referring to FIG. 5, the improved tooth cleaning device, additionally to the all described hereinabove elements, portions, etc., includes a fluid jet stream nozzle 30 instead of the bristle portion 23.

Figure 6:
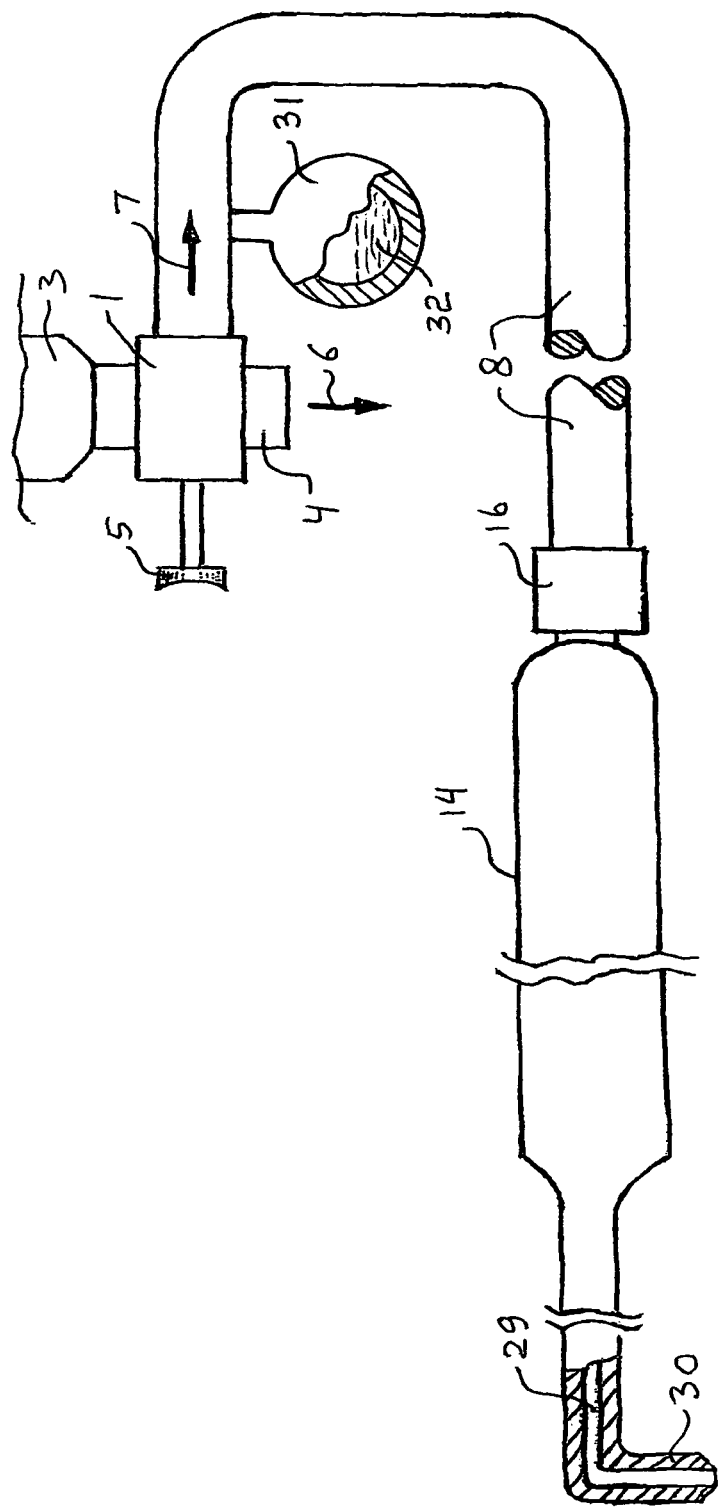
FIG. 6 is a simplified drawing of an improved tooth fluid jet stream cleaning device with the hygiene substance container.

FIG. 6 shows the hygiene substance container 31, attached to the improved tooth cleaning device. The container 31 is shown in FIG. 6 as of the spherical configuration, but it can be of any suitable configuration and geometric form. The hygiene substance 32 can be, for example a liquid such as a "Listerine", etc. The hygiene substance container 31, shown in FIG. 6, is located in the area of the controllable distributer 1, but it can be cut-in at any reasonable place of the improved tooth cleaning device. The hygiene substance container 31 is shown only in FIG. 6 related to the improved tooth cleaning device with the fluid jet stream nozzle 30 instead of the bristle portion 23, but the container 31 can be attached (not shown) to the improved tooth cleaning device having the brush portion 9 with head portion 20 comprising the bristle portion 23. When the hygiene substance container 31 is attached to the tooth cleaning device, the mixture of the fluid (water) with the hygiene substance (e.g., "Listerine", etc.) follow to the teeth during brushing, or during jet stream cleaning.

The improved tooth cleaning device provides at least two functions: the brush cleans a plaque from tooth surfaces and the fluid (jet stream) flushes away the plaque debris. The new improved device with a spray/stream eliminates the manual moisturizing of the tooth brush during tooth cleaning process, cleans a plaque from tooth surfaces, and flushes away the plaque debris. The fluid pressure (flow) can be controlled by sink/bath faucet's valve The coupling of the components (parts, portions, elements, etc.) of the improved tooth cleaning device can be provided by any other reasonable methods of their non-leaking connection each other.

The configuration and/or geometrical forms of the components (parts, portions, elements, etc.) of the improved tooth cleaning device, are not limited to the configuration and/or geometrical forms depicted in the FIGS. 1-6, and can be of any reasonable configuration and form, for instance, of any other regular (not shown) or of any reasonable irregular form/shape (not shown).

It is understood, that any other reasonable threaded or not treaded coupling or necessary rigid connections (not shown) can be used too. For example, the brush portion 9 is shown (FIGS. 1 and 2) as a solid piece of head 20 and handle 14 portions, but the brush portion 9 can be presented by to separate (not shown) head and handle portions rigidly (at least non-leakedly) connected each other. Also, the controllable distributer 1 can be mechanical or safely electrical, and can be of any principles of operation and/or control. The suitable controllable fluid distributer, offered for sale on the open market, can be used.

It is understandable, that the aperture 25 [or plurality of apertures (not shown)] can be of any reasonable regular or irregular configuration and forms.

Generalizing, any and all modifications of the invention within the scope of the claims are possible.

CONCLUSION, RAMIFICATION AND SCOPE

Accordingly the reader will see that, according to the invention, an improved tooth cleaning device is provided. An improved tooth cleaning device with a spray has various possibilities, considering activities of the tooth cleaning devices. While the above description contains many specificities, these should be not construed as limitations on the scope of the invention, but as exemplification of the presently-preferred embodiments thereof. An improved tooth cleaning device is universal and convenient for any tooth cleaning occasion. Also, such device eliminates the necessity of the manual moisturizing of the tooth brush during dental hygiene procedure.

Many other ramifications are possible within the teaching to the invention. For example, the device can be successfully used for jewelry cleaning, etc.

Thus, the scope of the invention should be determined by the appended claims and their legal equivalents, and not by examples given.

There has thus been outlined, rather broadly, the more important features of the invention. In this respect, it is understood that the invention is not limited in its application to the details of arrangements of the components/portions/elements set forth in the description and/or drawings. The invention is capable of other embodiments and of being practiced and carried out in various ways. Also, it is to be understood that the phraseology and terminology employed herein are for the purpose of description and should not be regarded as limiting.

While the above description contains many specificities, these should not construed as limitations on the scope of the invention, but as exemplification of the presently-preferred embodiments thereof. Many other ramifications are possible within the teaching to the invention.

The persons of ordinary skills and/or creativity in the art will readily observe that numerous modifications and advantages of the improved device may be made while retaining the teachings of the invention.

As such, those skilled in the art will appreciate that the conception, upon which this disclosure is based, can readily be utilized as a basis for the designing of other structures, for carrying out the several purpose of the present invention. It is important, therefore, that the claims be regarded as including such equivalent constructions insofar as they do not depart from the spirit and scope of the present invention.

THE DRAWING REFERENCE NUMERALS

1—a controllable fluid distributer;
2—a facet nozzle;
3—a sink facet;
4—a distributer nozzle;
5—a control organ;
6—a fluid first direction;
7—a fluid second direction;
8—a tubular portion (tube);
9—a brush portion;
10—a first connecting element;
11—a body of controllable distributer;
12—a first end of the tubular portion;
13—a second end of the tubular portion;
14—a handle portion;
15—a second connecting element;
16—a first pivotable nut;
17—an internal thread;
18—an external thread;
19—a projection of the handle portion;
20—a head portion;
21—an hollow body of the handle portion;
22—a head channel;
23—a bristle portion;
24—bristles;
25—an aperture;
26—a first connecting element channel;
27—a second connecting element channel;
28—a solid (not hollow) body of the handle portion;
29—a handle channel;
30—a hygiene substance container;
31—a hygiene substance;
32—a projection of the body of controllable distributer;
33—a third connecting element;
34—a second pivotable nut.

What is claimed is:

1. A tooth cleaning device comprising:

a control distributor adapted to be coupled to the nozzle of a sink faucet, said control distributor comprising a distributor nozzle for directing water flowing from the faucet to a sink adjacent the sink faucet, an opening on a side of the control distributor for directing the water flowing from the faucet out of the side of the control distributor, a switch for switching the water flow from flowing through the distributor nozzle to flowing through the opening and a first connecting element surrounding the opening;

a flexible tube having a first end sealingly coupled to the first connecting element and a second end; and a brush portion, said brush portion consisting of a handle portion, a head portion located at a first end of the handle portion wherein the head portion and the handle portion are formed as a one-piece element, a projection extending from a second end of the handle portion opposite the first end and a plurality of bristles extending from the head portion, the projection having a narrow flow channel therethrough, the handle portion being hollow and including a flow channel extending from the first end of the handle to the second end of the handle and in flow communication with the flow channel in the projection wherein the flow channel in the handle portion is wider than the flow channel in the projection, the head portion having a flow channel therethrough in fluid communication with the flow channel in the handle portion and at least one aperture positioned adjacent the bristles wherein the flow channel in the head portion is narrower than the flow channel in the handle portion;

a second connecting element connected to and surrounding the projection wherein the second end of the flexible tube is sealingly coupled to the second connecting element in order to enable water to flow from the distributor nozzle to the brush portion and out of the at least one aperture; and a hygiene substance container having a hygiene substance therein positioned on the flexible tube in order to enable the hygiene substance to enter the water flowing through flexible tube.

* * * * *